(12) United States Patent
Marsh

(10) Patent No.: US 10,575,919 B2
(45) Date of Patent: Mar. 3, 2020

(54) CONNECTOR FOR A SURGICAL LIGHTING SYSTEM

(71) Applicant: Kim A. Marsh, Naples, FL (US)

(72) Inventor: Kim A. Marsh, Naples, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 0 days.

(21) Appl. No.: 16/405,241

(22) Filed: May 7, 2019

(65) Prior Publication Data

US 2019/0336239 A1 Nov. 7, 2019

Related U.S. Application Data

(60) Provisional application No. 62/667,754, filed on May 7, 2018.

(51) Int. Cl.
*A61B 90/30* (2016.01)
*A61B 90/50* (2016.01)
*F21V 33/00* (2006.01)
*A61B 17/00* (2006.01)
*F21W 131/205* (2006.01)

(52) U.S. Cl.
CPC ............ *A61B 90/30* (2016.02); *A61B 90/50* (2016.02); *F21V 33/0068* (2013.01); *A61B 17/00234* (2013.01); *A61B 2017/0023* (2013.01); *A61B 2090/306* (2016.02); *F21W 2131/205* (2013.01)

(58) Field of Classification Search
CPC ..... A61B 90/35; A61B 17/02; A61B 17/0206; A61B 17/3211; A61B 17/3213; A61B 17/3215; F21V 21/0885; F21L 4/04
See application file for complete search history.

(56) References Cited

U.S. PATENT DOCUMENTS

| 4,605,990 A * | 8/1986 | Wilder | A61B 1/32 24/507 |
| 8,317,693 B2 * | 11/2012 | Grey | A61B 90/35 600/212 |
| 2016/0100897 A1 * | 4/2016 | Avalos | A61B 17/0206 600/411 |

\* cited by examiner

*Primary Examiner* — Anne M Hines
(74) *Attorney, Agent, or Firm* — William E. Noonan

(57) ABSTRACT

A surgical lighting system includes a connector for communicably joining a light carrier to a fiberoptic cable. The connector includes an inlet section having a receptacle for operatively engaging a light discharge outlet of the fiberoptic cable. A chuck mechanism includes a body that is rotatably interconnected with the inlet section. The chuck body has a passageway that communicates with the outlet of the fiberoptic cable engaged with the receptacle of the inlet section. The chuck mechanism also includes a set of adjustable jaws that are selectively opened and closed by turning a cap attached to the chuck body. Opening the jaws exposes the passageway through the chuck mechanism. The light carrier is engaged with the exposed passageway and the jaws are closed to grip the light carrier and communicably connect the fiberoptic cable to the light carrier.

14 Claims, 4 Drawing Sheets

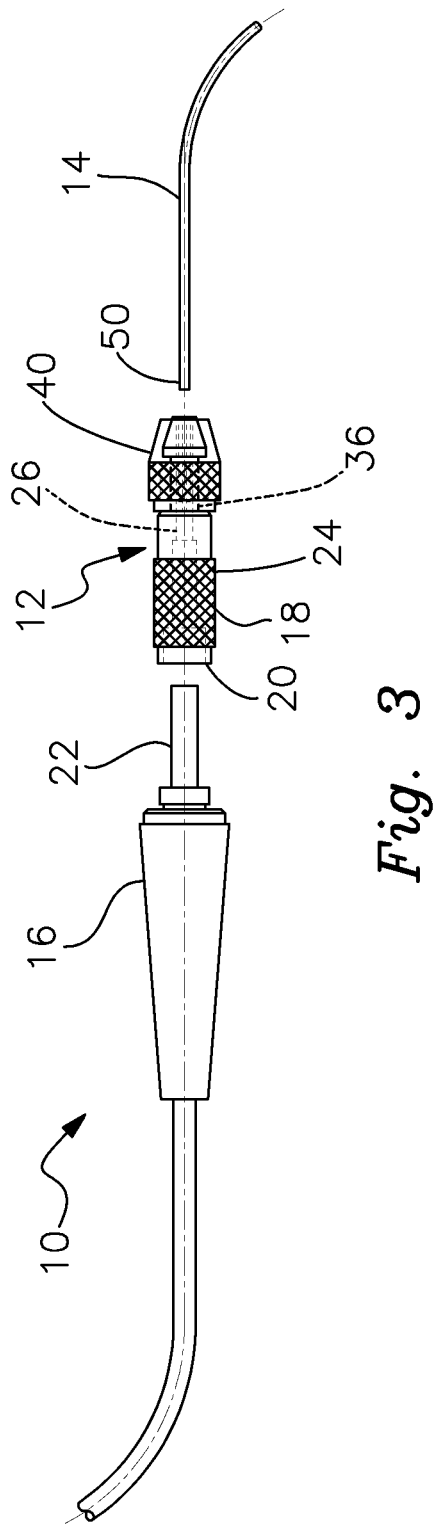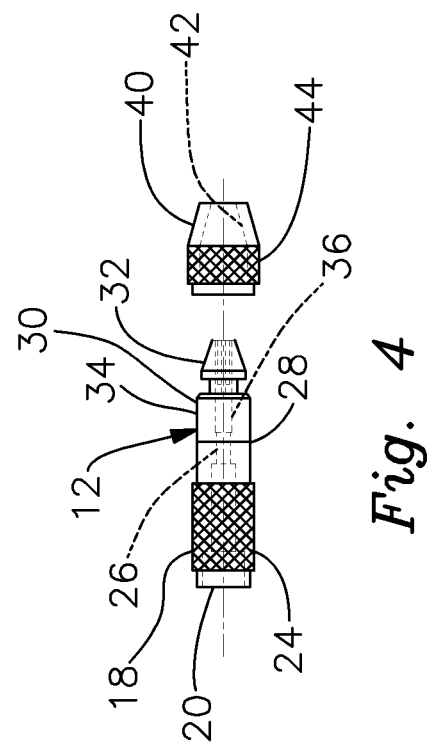
Fig. 3
Fig. 4

CONNECTOR FOR A SURGICAL LIGHTING SYSTEM

FIELD OF THE INVENTION

This invention relates to a surgical lighting system employed to illuminate various medical and surgical procedures. More particularly, the invention relates to a connector for releasably securing an illuminating light carrier to a standard fiberoptic cable.

BACKGROUND OF THE INVENTION

Various types of lighting systems are currently available for use with lighted medical and surgical scopes including, for example, ENT scopes, laparoscopes, endoscopes, etc. Typically, in such lighting systems, the light inlet of a standard fiberoptic cable is connected to an illuminator or other type of light source. The opposite, outlet end of the fiberoptic cable is attached to a standard rigid glass fiber light carrier, which is itself encased and fused within an elongate metal sleeve or tube. This sleeve is sized and configured to fit snugly in a channel of the scope that is being utilized. Light is directed from a distal output end of the light carrier and discharged from the channel of the scope to illuminate a particular medical or surgical procedure.

The surgical lighting system described above exhibits a number of limitations and disadvantages. Because the light carrier is secured within a rigid metal casing, its use is normally limited to only a single type of scope, as well as a scope that has a specific corresponding size and configuration. Conventional light carriers are not versatile and cannot be used with the wide variety of medical and surgical scopes that are currently available. A separate and distinct light carrier is usually required for each different size and type of surgical instrument. The metal casing can also present problems because, during use, it is apt to transmit heat generated by the light carrier. This can make the scope difficult to handle, which is likely to interfere with or complicate the surgical or medical procedure being performed. Scopes featuring the known light carrier can also be difficult to clean and sanitize. The rigid carrier tends to trap blood within the channel of the scope. This can cause the build up of contaminants which can be troublesome to remove.

SUMMARY OF THE INVENTION

It is therefore an object of the present invention to provide an improved, versatile surgical lighting system that may be used effectively on assorted scopes of various types, configurations or sizes for illuminating medical and surgical procedures.

It is a further object of this invention to provide a surgical lighting system featuring a unique gripping connector that enables fiberoptic light carriers of various lengths and diameters to be used interchangeably so that the system is not limited to use with a scope of a particular size or type, but rather may be used in a much more versatile and efficient manner with a wide variety of medical and surgical instruments.

It is a further object of this invention to provide a surgical lighting system that greatly reduces the expense and inconvenience of having to maintain a large inventory of lighting systems having different sizes and configurations.

It is a further object of this invention to provide a surgical lighting system featuring a light carrier that is not encased in a metal sleeve or tubing and which is therefore much easier and more effective to use in scopes having various different sizes and configurations.

It is a further object of this invention to provide for a surgical lighting system that effectively and reliably directs and focuses light without the accompanying and potentially disruptive heat transmission exhibited by standard surgical lighting systems.

It is a further object of this invention to provide for a surgical lighting system that eliminates the use of a rigid light carrier having a precise size and configuration required for a specific scope and instead employs a flexible light carrier that may be readily sized and configured to extend through and/or fit on surgical scopes and instruments having various sizes and configurations.

It is a further object of this invention to provide for a surgical lighting system that illuminates surgical and medical procedures more reliably and effectively than existing systems and which blocks light from being scattered or directed in a manner that could distract medical personnel and potentially disrupt the procedure being illuminated.

It is a further object of this invention to provide for a surgical lighting system that may be conveniently mounted to a scope, either internally through an integral channel of the scope or externally by clips or fasteners attached to the scope.

It is a further object of this invention to provide a surgical lighting system featuring a variety of differently configured light carriers that may be selectively interchanged to provide for the type of lighting required for a particular surgical or medical procedure.

It is a further object of this invention to provide a surgical lighting system employing a flexible and disposable light carrier that greatly facilitates cleaning and sterilization of both the lighting system and surgical scopes using the lighting system.

This invention features a surgical lighting system for use in a scope or other instrument to illuminate a surgical or other medical procedure. The system includes a connector for releasably interconnecting a light discharge outlet of a fiberoptic cable with a light carrier. More particularly, the connector includes an inlet section that has a receptacle for releasably receiving the light discharge outlet of the fiberoptic cable. A chuck mechanism includes a cylindrical chuck body that is rotatably interconnected to the inlet section. A central passageway formed through the chuck body communicates with the receptacle of the inlet section. The chuck mechanism further includes a plurality of radially adjustable jaws that extend from a distal end of the chuck body. A cap is operatively attached to the chuck mechanism such that axially rotating the cap in a first direction radially opens the jaws of the chuck mechanism and axially rotating the cap in an opposite second direction closes the jaws of the chuck mechanism. When the jaws of the chuck mechanism are open, the interior passageway of the chuck mechanism is exposed for receiving or otherwise engaging a light entry of the light carrier. When the jaws are closed, they engage and grip the light carrier to hold the light carrier so that a light inlet end of the light carrier is communicably aligned with the light outlet end of the fiberoptic cable received by the receptacle of the inlet section. This allows light discharged from the fiberoptic cable to be transmitted through the connector to the light entry of the light carrier. The light carrier then transmits the light therethrough and projects the transmitted light therefrom to illuminate a medical or surgical procedure.

In a preferred embodiment, the inlet section of the connector may have a central bore that is aligned with the passageway formed through the body of the chuck mechanism. The central bore interconnects the receptacle of the inlet section and the passageway formed through the chuck body. The inlet section and the cap may include respective knurled circumferential surfaces that facilitate rotation of the cap and the attached chuck mechanism relative to the inlet section of the connector.

The light carrier may have various selected lengths and flexibilities. A portion of the light carrier may be covered by sheathing. Such sheathing may include a plastic overmold. The light carrier may be received through the channel of a scope or other surgical instrument. Alternatively, the light carrier may be dipped or otherwise releasably fastened to the outside or external surface of the scope or other instrument.

BRIEF DESCRIPTION OF THE DRAWINGS

Other objects, features and advantages will occur from the following description of a preferred embodiment and the accompanying drawings, in which:

FIG. 3 is an exploded side view of a preferred surgical lighting system according to this invention;

FIG. 4 is an exploded side elevational view of the preferred connector of this invention with the cap detached from the remainder of the connector to depict the chuck mechanism;

DETAILED DESCRIPTION OF PREFERRED EMBODIMENTS

Figure 1:
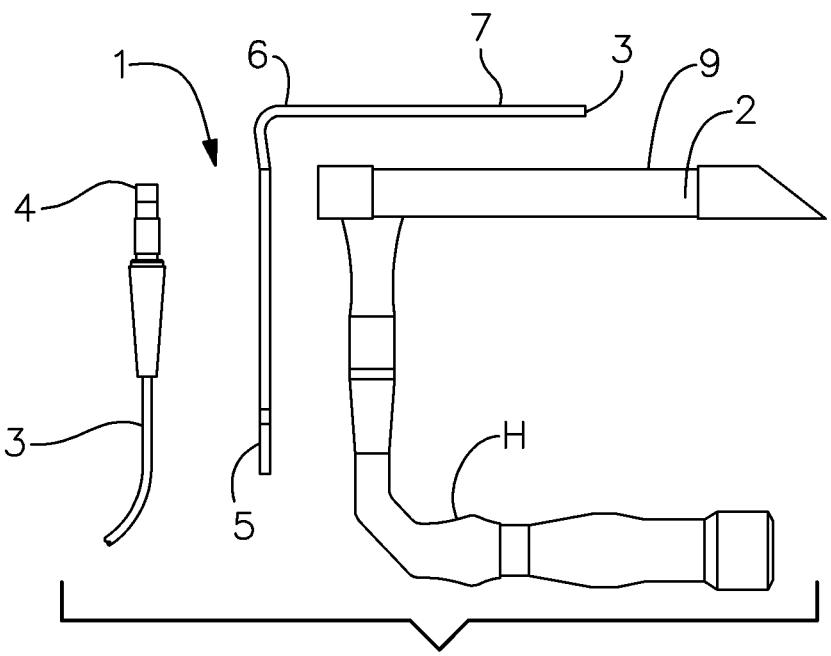
FIG. 1 is a plan view of a laryngoscope in a disassembled condition, which employs a lighting system according to the prior art.
Figure 2:
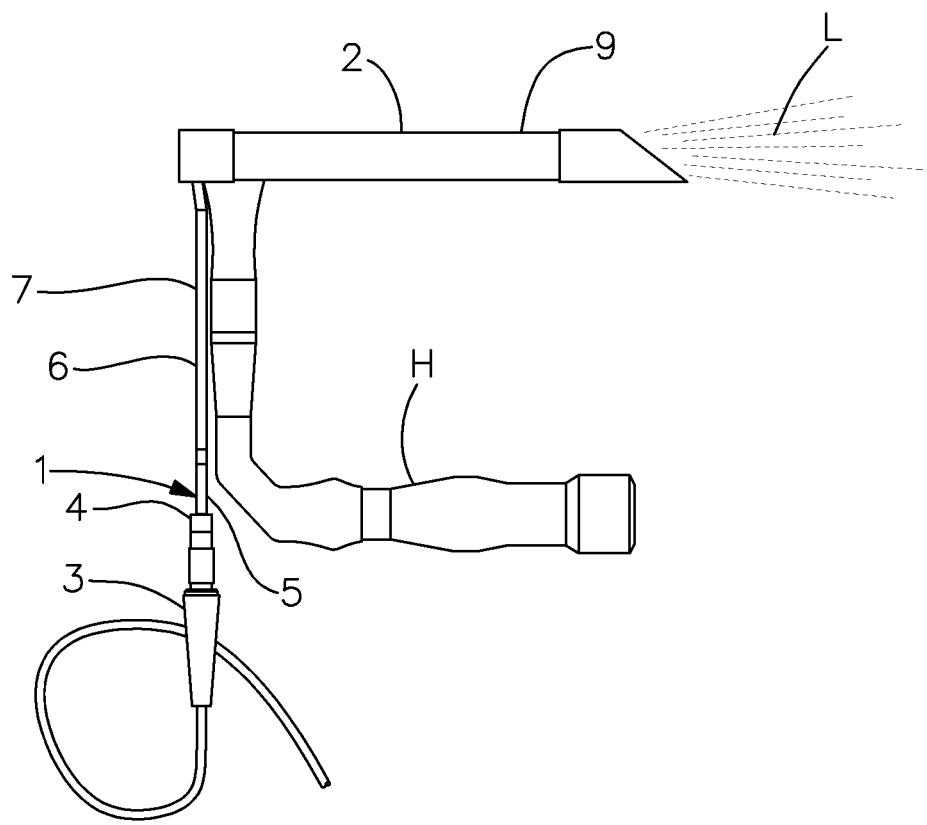
FIG. 2 is plan view of an assembled laryngoscope using the lighting system of the prior art and being operated to provide illumination for a medical or surgical procedure.

There is shown in FIGS. 1 and 2 a surgical lighting system of the type conventionally employed for medical instruments. Such instruments typically comprise scopes designed to illuminate various sorts of medical procedures. These can include, but are not limited to laryngoscopes, laparoscopes, ENT scopes and endoscopes. It should be understood that the type of scope or medical instrument with which the invention may be employed is not a limitation of this invention.

FIGS. 1 and 2 depict a conventional lighting system 1 as used with a representative laryngoscope 2. Lighting system 1 features a standard fiberoptic cable 3 that is operatively connected in a known manner at an inlet end (not shown) to a fiberoptic illuminator or other light source, which will be well known to persons skilled in the art. A standard light discharge or outlet fitting 4 of cable 3 is communicably connected to an inlet end 5 of a generally L-shaped light conducting component 6. As is known in the prior art, light conducting component 6 comprises a standard light fiber, which is obscured and not shown, encased within a metal sleeve or tube 7. An outlet end 8 of sleeve 7 is open to expose a distal discharge end of the encased light conducting fiber.

Laryngoscope 2 features an elongate interior channel formed through tubular upper member 9. The tubular upper member is itself supported on a 90° angle handle H. Each end of the interior channel formed through member 9 is open. When the scope is fully assembled, as shown in FIG. 2, casing 7 of light conducting element 6 is received by tubular member 9 and installed within laryngoscope 2. More particularly, inlet fitting 5 is attached to the outlet fitting 4 of the fiberoptic cable. As a result, the light fiber within casing 7 is placed in optical communication with the fiberoptic cable 3. The generally horizontal segment of light conducting piece 6 is inserted through the interior channel of laryngoscope member 9. As a result, when the fiberoptic illuminator is actuated, light is transmitted through the fiberoptic cable and through the encased optical fiber. The light is then discharged from a distal end of the fiber and projected from the laryngoscope as light L. This light is then directed toward and illuminates a related medical or surgical procedure.

It should be understood that various other types of scopes and illuminated medical instruments commonly feature different sizes and configurations. In each such system, a corresponding metal encased light conducting piece must be specifically sized and configured to fit operatively onto or within the instrument. Accordingly, a differently sized and/or configured light conducting piece 6 is required for virtually each different type, size and configuration of scope or instrument. This requires the hospital, surgical center and/or medical practice to maintain an unduly large assortment of metal encased, light conducting fibers/carriers for use with the many different types of scopes and instruments that require illumination. A light conducting piece such as piece 6 shown in FIGS. 1 and 2 does not normally fit instruments having other shapes and sizes. In addition, the metal casing 7 transmits heat from the encased fiber, which can distract the user and potentially disrupt the medical or surgical procedure being illuminated.

FIG. 3 depicts a surgical lighting system 10 in accordance with this invention which addresses and overcomes the foregoing difficulties. In particular, system 10 includes a connector 12, shown alone in FIG. 4, which operatively and releasably interconnects a light carrier 14 to a fiberoptic cable 16.

Light carrier 14 preferably comprises any of various types of light conducting and projecting materials, which will be known to persons skilled in the art. These may include either rigid or preferably flexible medical grade glass or plastic elements.

Carrier 14 may have various degrees of flexibility or may alternatively comprise a rigid material, which is suited for the particular configuration and mounting location of the scope to which the system is attached. Fiberoptic cable 16 may comprise virtually any type of fiberoptic cable including various standard cables that are used for medical illumination. It should be understood that the light inlet end and related fitting of cable 16, not shown, are attached, as previously described, to a fiberoptic illuminator, which is operated during use of the system to transmit light through cable 16.

As previously indicated, cable 16 is operatively and releasably interconnected to light carrier 14 by connector 12. The connector of system 10 includes a generally cylindrical inlet section 18 having an inlet receptacle 20 for operatively and communicably receiving a light discharge outlet 22 of cable 16. An enlarged knurled surface 24 is formed circumferentially about inlet section 18. A central bore 26 extends through inlet section 18 from receptacle 20 to the distal end 28 of the inlet section.

A chuck mechanism 30 for releasably gripping light carrier 14 is rotatably and operatively interconnected with the distal end of inlet section 18. Chuck mechanism 30 may be constructed in accordance with known manufacturing techniques and structural elements as used, for example, by the tool industry in the manufacture of drill chucks and analogous gripping devices. In particular, chuck mechanism 30 includes a cylindrical chuck body 34 and multiple (typically three or four) radially adjustable jaws 32 that are operatively interengaged with cylindrical chuck body 34 in a known manner (e.g. by interengaged threads) such that when the chuck body 34 is rotated in a first (e.g. counterclockwise) direction the jaws radially or diametrically open and, conversely, when chuck body 34 is axially rotated in the opposite (e.g. clockwise) direction, jaws 32 radially or diametrically close. This allows the jaws 32 of chuck mechanism 30 to selectively grip and hold light carrier 14 in a manner that will be described more fully below.

Cylindrical chuck body 34 includes a central passageway 36 that communicates with bore 26 of inlet section 18. Passageway 36 extends fully through chuck body 34 such that when the jaws 32 are open, passageway 36 is exposed through the jaws 32.

Connector 12 further includes a sleeve or cap 40 that is fixedly attached to chuck body 34. Cap 40 includes an interior recess 42 that snugly and fixedly receives the chuck mechanism. In particular, a cylindrical entrance to recess 42 conforms to the circumference of chuck body 34. Recess 42 then tapers toward a distal end of the cap to generally correspond to the tapered outer circumferential surfaces of jaws 32. Cap 40 is secured tightly enough to chuck body 34 so that rotating cap 40 will cause chuck body 34 to rotate either clockwise or counterclockwise as desired. To facilitate turning of the chuck body, cap 40 is provided with a knurled outer surface 44. The tapered opening in the cap snugly engages the tapered outer circumferential surfaces of jaws 32, at least when the jaws are in an open condition. When the jaws are closed there is clearance provided between the tapered circumferential surfaces of the jaws and the tapered interior surface of the cap.

In operation, fiberoptic cable 16 is attached to connector 12 by inserting discharge outlet 22 of cable 16 into receptacle 20 of inlet section 18. Cap 40 is then turned in a counterclockwise direction. This rotates chuck body 34, which in turn, opens jaws 32 of chuck mechanism 30. This exposes interior passageway 36, which is generally aligned and communicates with bore 26 of inlet section 18. The doctor or other medical personnel using system 10 selects a desired light carrier 14 for the particular surgical procedure involved and inserts a light entry end 50 of light carrier 14 through the open jaws 32 and into passageway 36 of chuck body 34. The user then grasps the knurled section 34 of cap 40 and rotates the cap in a clockwise direction to close the jaws. The jaws securely grip light carrier 14 and hold the light carrier in secure interengagement with connector 12.

Light carrier 14 may include either a focused or flared/angled distal end or tip. A flared or angled end is utilized to provide a broadcast or wider lighting pattern. A focused tip is utilized to provide narrowed or more direct lighting. The shape of the carrier's end tip may be varied and selected by the user in order to achieve the lighting effect needed for a particular application.

The medical or surgical procedure is illuminated by actuating the fiberoptic illuminator. Light is transmitted through cable 16 and discharged from outlet end 22. This light is transmitted through bore 26 of inlet section 18 and through communicating interior passageway 36 of chuck mechanism 30 to light entry end 50 of interengaged light carrier 14. Bore 26 and passageway 36 may have multiple segments with different respective diameters or alternatively may feature a uniform diameter. The light carrier then transmits and projects the light toward the surgical or medical site to be illuminated.

Figure 5:
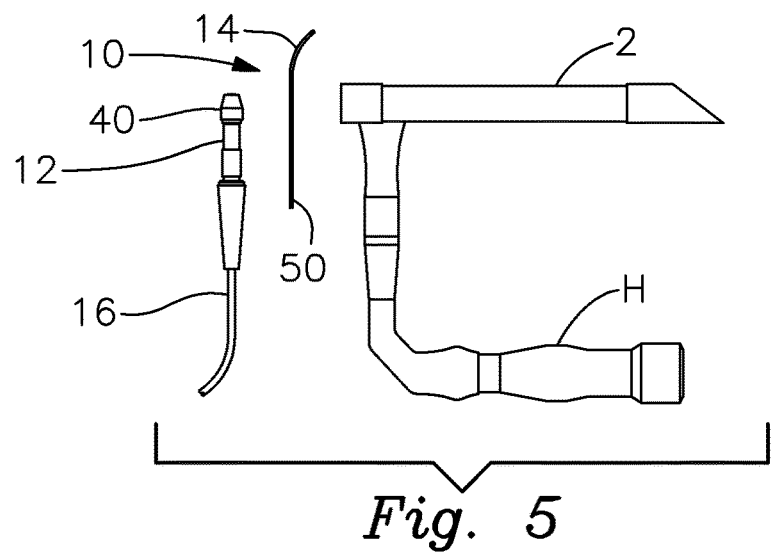
FIG. 5 is a plan view of disassembled laryngoscope, which utilizes the lighting system of this invention.
Figure 6:
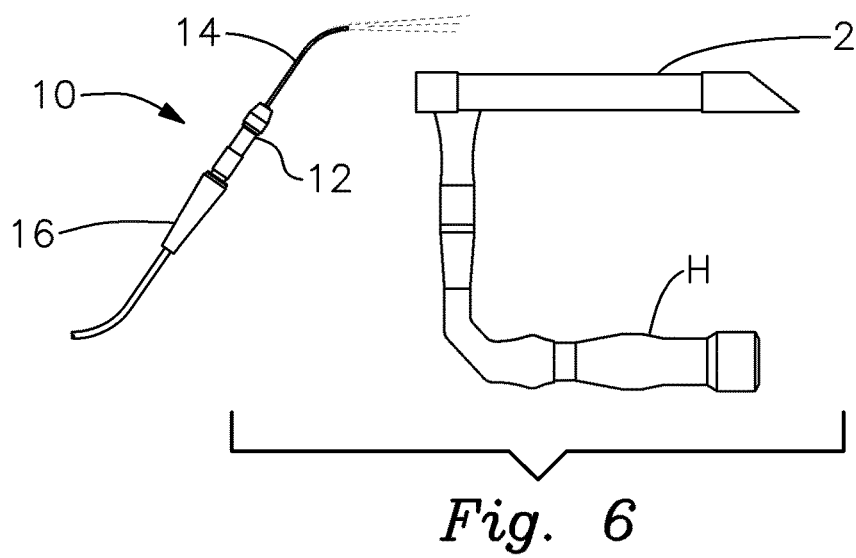
FIG. 6 is a plan view of the assembled lighting system as described herein; the lighting system is shown removed from the laryngoscope with which the lighting system is to be used.
Figure 7:
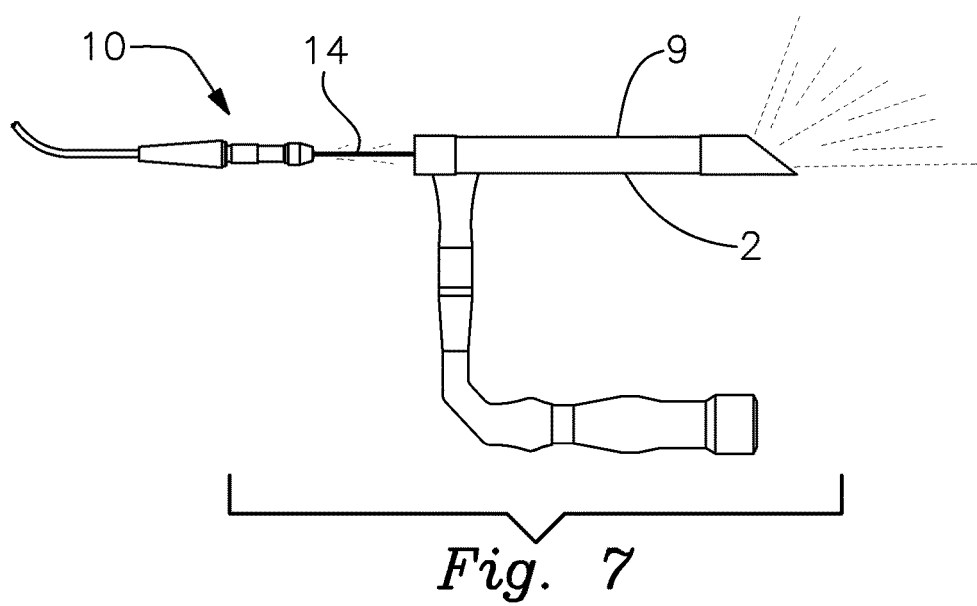
FIG. 7 is a plan view showing the lighting system operatively engaged with the laryngoscope to illuminate a surgical procedure.

FIGS. 5-7 show lighting system 10 interengaged with the previously described laryngoscope 2. Specifically, fiberoptic cable 16 is operatively interengaged with the inlet section of connector 12. The opposite end of connector 12 releasably grips a selected light carrier 14 as described above. In FIG. 5, light carrier 14 is shown detached from connector 12. As previously described, the jaws of the connector's chuck mechanism are opened by turning cap 40, typically in a counterclockwise direction. Carrier 14 is then inserted through the jaws and into the previously described passageway 36 (FIG. 3) of the chuck mechanism such that the light entry 50 of carrier 14 is optically communicably connected to the light discharge outlet 22 of fiberoptic cable 16.

As illustrated in FIG. 6, after the light carrier 14 is attached to connector 12, the fiberoptic illuminator (not shown) may be actuated to transmit light through the fiberoptic cable 16 and connector 12 to light carrier 14. Lighting system 10 is then quickly and easily engaged with laryngoscope 2 simply by inserting light carrier 14 through the conventional interior channel in upper member 9 of laryngoscope 2. The light carrier 14 of system 10 may be just as conveniently interengaged with or otherwise connected to various other scopes and medical instruments. In scopes that include an elongate channel for conventionally receiving a metal encased conducting fiber, the fiber 14, which is not encased in metal, may be inserted and flexed or bent, if necessary, to slide through virtually any channel diameter or configuration. In alternative scopes, a rigid light carrier 14 may be employed. Moreover, the light carrier may be attached to an outer or external surface of the scope or other medical instrument and secured thereto by appropriate clips or fasteners. In any event, the lighting system 10 shown in FIGS. 3-7 may be employed with a wide assortment of scopes and medical instruments having many different sizes and configurations.

The length of light carrier 14 may simply be adjusted as needed for a particular surgical/medical application or size of scope. The carrier may be cut or otherwise adjusted by the user to meet their requirements. Color coding, indentations or other forms of marking may be applied to carrier to indicate particular lengths or measurements. The length of the carrier needed for a particular scope can be achieved, for example, by cutting or breaking/snapping the carrier of a corresponding indentation or other marking on the carrier. The light carrier may also have various diameters and degrees of flexibility as required for certain applications. Quite significantly, by employing the system of this invention, multiple types of scopes and medical instruments can employ a single lighting system 10 employing an easily interchangeable light carrier which may selected for the particular scope and surgical or medical procedure involved. In contrast to the prior art, each different type of scope does not require its own corresponding lighting system. The medical practitioner or facility is therefore not required to maintain such a large inventory of lighting systems having different shapes and sizes.

Figure 8:
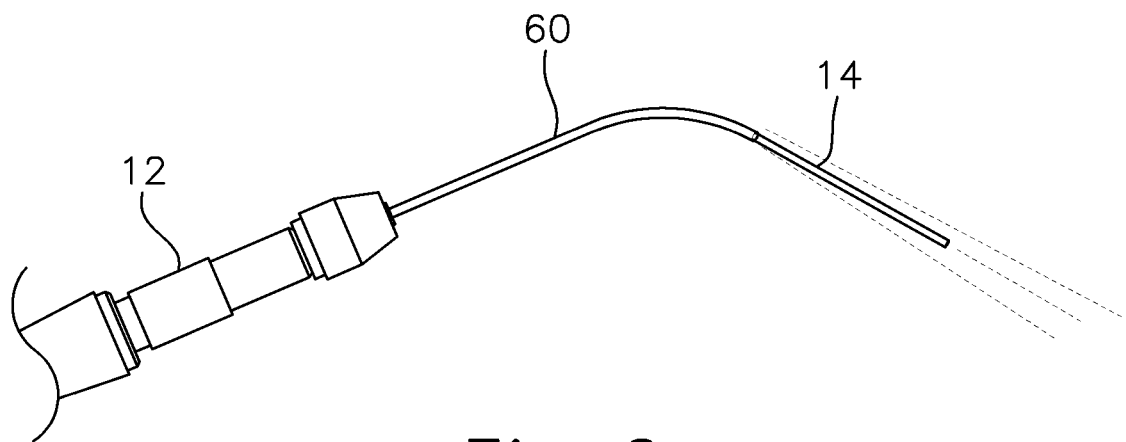
FIG. 8 is an elevational side view of the lighting system with sheathing formed along a section of the light carrier and extending from the connector such that illumination is projected only from the exposed portion of the light carrier extending beyond the sheathing.
Figure 9:
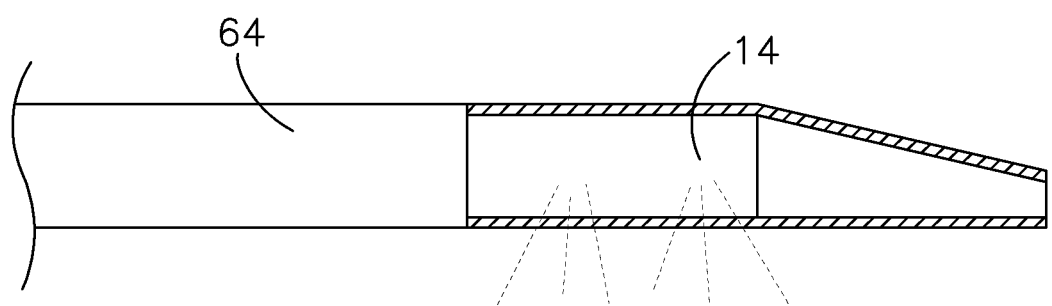
FIG. 9 is an elevational side view of the light carrier partially covered by a sheathing; in particular, the distal segment of the sheathing covers approximately a 180° circumferential segment of the light carrier so that light is directed only from the exposed section of the light carrier.

As shown in FIGS. 8 and 9, certain versions of this invention may employ a plastic or overmold sheathing 60, 64 respectively for covering different parts or sections of light carrier 14. In FIG. 8, sheathing 60 extends from connector 12 for a part of the length of light carrier 14. Sheathing 60 fully surrounds the light carrier such that only a distal section 62 of tight carrier 14 is exposed and light is projected from that exposed section 62. Light is blocked from being projected from the remaining covered portion of the light carrier. In FIG. 9, the sheathing 64 entirely surrounds a portion of light carrier 14 but covers only about ½ or a 180° circumferential segment of the light carrier proximate the distal end of the light carrier. As a result, approximately a 180° circumferential section of light carrier 14 is exposed and light is directed from that exposed section onto a selected area of the surgical site. The configuration of the sheathing can be varied in this manner to project and direct light from the light carrier as required for a particular operation.

Not only does the present invention provide much greater versatility and efficiency, it also eliminates the use of a metal casing and the resulting heat transmission exhibited by prior art lighting systems. Light carriers having various lengths, configurations, diameters and thicknesses may be quickly, conveniently and interchangeably used with the lighting system so that the system is adaptable for use with virtually any type of illuminated scope or medical instrument. This provides a capability that has been lacking with the prior art.

In contrast to conventional lighting systems for use in surgical scopes, the present invention employs a disposable, flexible light carrier. Greater clearance is provided between the carrier and the scope channel accommodating the carrier then is provided by rigid light carriers of the prior art. The flexible fiber carrier is much less apt to trap blood and other contaminants in the channel and may be quickly and easily removed from the scope without pulling undue amounts of blood into the channel or the scope. Moreover, the light carrier is disposed of after each use. This makes it much easier to clean and sanitize the scope and the lighting system.

Changing the light carrier as needed is quick and convenient. The unique and easy-to-use chuck mechanism not only allows the light carrier to be readily changed, it also holds the light carrier securely in place during use. In addition, the light carrier is optically interengaged with the fiberoptic cable in a highly effective and reliable manner so that light losses are mitigated and light is more effectively transmitted to the light carrier and projected onto the surgical site. Improved surgical illumination and lighting system versatility are thereby achieved.

The connector, light carrier and fiberoptic cable may employ various materials within the scope of this invention. Assorted types of medical grade metal, glass and plastic may be incorporated into the component parts of the lighting system. The connector preferably comprises titanium, steel or other medical grade metals/metal alloys. The particular types of materials do not constitute a limitation of this invention.

Connector 12 may likewise feature various sizes, configurations and dimensional tolerances. For example, the jaws may employ a gap ranging from about 1 mm to 3.5 mm for enabling the connector to securely grip different sizes and types of light carriers. Nevertheless, alternative dimensional tolerances may be exhibited within the scope of the invention.

Accordingly, this invention provides for a lighting system especially suited for use in medical and surgical scopes and, more particularly, to a connector for operatively joining a fiberoptic cable to a selected one of a wide variety of light carriers suited for use in surgical and medical applications. Although specific features of the invention are shown in some of the drawings and not others, this is for convenience only, as each feature may be combined with any and all of the other features in accordance with this invention.

What is claimed is:

1. In a lighting system for use in a surgical instrument to illuminate a surgical or medical procedure, which lighting system includes a fiberoptic cable connected at one end to a light source and having a light discharge outlet at an opposite end thereof, the lighting system also including a light carrier having a light entry and a communicably connected light projecting surface, the improvement comprising:

a connector for releasably and communicably interconnecting the light outlet section of a fiberoptic cable with the light entry of the light carrier, said connector including an inlet section for releasably and communicably engaging the light discharge outlet of the fiberoptic cable, a chuck mechanism having a cylindrical chuck body rotatably interconnected to said inlet section, said chuck body including an interior passageway formed therethrough, which passageway communicates with said inlet section, said chuck mechanism further including a plurality of radially adjustable jaws that extend from a distal portion of said chuck body and a cap operatively attached to said chuck mechanism and axially rotatable in a first direction to radially open said jaws of said chuck mechanism, said cap being axially rotatable in an opposite second direction to close said jaws of said chuck mechanism such that, when said jaws of said chuck mechanism are open, said interior passageway of said chuck mechanism is exposed for communicably interengaging the light entry of the light carrier, said jaws of said chuck mechanism being selectively closed for gripping and holding the light carrier so that the light entry of the light carrier is communicably aligned with the light discharge outlet of the fiberoptic cable engaged with said inlet section to allow light discharged from the fiberoptic cable to be transmitted through said central passageway of the chuck mechanism to the light entry of the light carrier, whereby the light carrier transmits the light therethrough and projects the transmitted light to illuminate a medical or surgical procedure.

2. The device of claim 1 in which said inlet section of said connector includes a central bore that is aligned with said passageway to communicably interconnect said inlet section and said passageway.

3. The device of claim 1 in which said cap is fixedly attached to said chuck body and said inlet section and said cap include respective knurled circumferential surfaces that facilitate rotation of said cap and said attached chuck body relative to said inlet section of said connector.

4. The device of claim 1 in which said inlet section includes a receptacle for receiving the light discharge outlet of the fiberoptic cable.

5. The device of claim 1 in which said cap is fixedly attached to said chuck body and said inlet section and said cap include respective knurled circumferential surfaces that facilitate rotation of said cap and said attached chuck body relative to said inlet section of said connector.

6. The device of claim 1 in which said inlet section includes a receptacle for receiving the light discharge outlet of the fiberoptic cable.

7. A connector for use in a surgical lighting system, which system includes a fiberoptic cable having a first end connected to a light source and an opposite second end having a light discharge outlet, the surgical lighting system further including a light carrier having a light entry and a communicably connected surface for projecting light therefrom, said connector comprising:
 an inlet section having a receptacle for releasably receiving the discharge end of a fiberoptic cable;
 a chuck mechanism including a cylindrical chuck body rotatably interconnected to said inlet section, said chuck body having a central passageway formed therethrough, which passageway communicates with said receptacle of said inlet section, said chuck mechanism further including a plurality of radially adjustable jaws that extend from a distal portion of said chuck body; and
 a cap operatively attached to said chuck mechanism and axially rotatable in a first direction to radially open said jaws of said chuck mechanism, said cap being axially rotatable in an opposite second direction to close said jaws of said chuck mechanism such that, when said jaws of said chuck mechanism are open, said interior passageway of said chuck mechanism is exposed for receiving the light entry of the light carrier, said jaws of said chuck mechanism being selectively closed for gripping and holding the light carrier so that the light entry of the light carrier is communicably aligned with the light outlet of the fiberoptic cable received by said receptacle of said inlet section, which allows light discharged from the fiberoptic cable to be transmitted through said passageway of said chuck mechanism and received by the light entry of the light carrier, whereby the light carrier transmits and projects the received light to illuminate a medical or surgical procedure.

8. The connector of claim 7 in which said inlet section of said connector includes a central bore that is aligned with said passageway to communicably interconnect said inlet section and said passageway.

9. The connector of claim 7 in which said cap is fixedly attached to said chuck body and said inlet section and said cap include respective knurled circumferential surfaces that facilitate rotation of said cap and said fixedly attached chuck body relative to said inlet section of said connector.

10. A surgical lighting assembly for use in a surgical instrument to illuminate a surgical or other medical procedure, which lighting system is for use in combination with a fiberoptic cable that is operatively connected to a light source and has a light discharge outlet, said system comprising:
 a light carrier having a light entry and a communicably connected light projecting surface; and
 a connector for releasably interconnecting the light discharge outlet of the fiberoptic cable with said light entry of said light carrier, said connector including an inlet section for releasably and communicably interengaging the discharge outlet of the fiberoptic cable, a chuck mechanism including a cylindrical chuck body rotatably interconnected to said inlet section, said chuck body having a central passageway formed therethrough, which passageway communicates with said receptacle of said inlet section, said chuck mechanism further including a plurality of radially adjustable jaws that extend from a distal portion of said chuck body, and a cap operatively attached to said chuck mechanism and being axially rotatable in a first direction to radially open said jaws of said chuck mechanism, said cap being axially rotatable in an opposite second direction to close said jaws of said chuck mechanism such that, when said jaws of said chuck mechanism are open, said interior passageway of said chuck mechanism is exposed for communicably interengaging the light inlet of the light carrier, said jaws of said chuck mechanism being selectively closed for gripping and holding the light carrier so that the light entry of the light carrier is communicably aligned with the light discharge outlet of the fiberoptic cable interengaged with said inlet section to allow light discharged from the fiberoptic cable to be transmitted through the central passageway of the chuck mechanism and received by said entry of said light carrier, whereby said light carrier transmits and projects the received light to illuminate a medical or surgical procedure.

11. The device of claim 10 in which said inlet section of said connector includes a central bore that is aligned with said passageway to communicably interconnect said inlet section and said passageway.

12. The device of claim 10 in which at least a portion of said light carrier is covered by a sheathing to partially restrict the projection of light therefrom.

13. The device of claim 12 in which the light carrier has an elongate shape and said sheathing is wrapped circumferentially about said light carrier and extends partially and not fully along the length of said light carrier to expose a distal segment of said light carrier for illuminating a medical or surgical procedure.

14. The device of claim 12 in which said light carrier has an elongate shape and said sheathing extends fully along the length of said light carrier and wherein a longitudinal gap is formed in said sheathing such that light is projected from said light carrier in a predetermined direction through said gap.

* * * * *